United States Patent
Heeren et al.

(10) Patent No.: US 9,579,017 B2
(45) Date of Patent: Feb. 28, 2017

(54) TRACKING SYSTEM FOR SURGICAL OPTICAL COHERENCE TOMOGRAPHY

(71) Applicant: NOVARTIS AG, Basel (CH)

(72) Inventors: Tammo Heeren, Aliso Viejo, CA (US); Lingfeng Yu, Rancho Santa Margarita, CA (US)

(73) Assignee: Novartis AG, Lichtstrasse, Basel (CH)

(*) Notice: Subject to any disclaimer, the term of this patent is extended or adjusted under 35 U.S.C. 154(b) by 31 days.

(21) Appl. No.: 14/739,726

(22) Filed: Jun. 15, 2015

(65) Prior Publication Data
US 2016/0360959 A1    Dec. 15, 2016

(51) Int. Cl.
| A61B 3/12 | (2006.01) |
| A61B 3/10 | (2006.01) |
| A61B 3/00 | (2006.01) |
| A61B 3/14 | (2006.01) |
| A61B 3/13 | (2006.01) |
| A61F 9/007 | (2006.01) |

(52) U.S. Cl.
CPC ............ *A61B 3/102* (2013.01); *A61B 3/0025* (2013.01); *A61B 3/0033* (2013.01); *A61B 3/12* (2013.01); *A61B 3/13* (2013.01); *A61B 3/14* (2013.01); *A61F 9/007* (2013.01)

(58) Field of Classification Search
CPC .. A61B 3/102; A61B 3/12; A61B 3/14; A61B 3/1025; A61B 5/0066; A61B 2090/3735; A61B 3/1208; A61B 3/13; A61B 90/00
USPC ................. 351/221, 206, 246, 205; 600/425
See application file for complete search history.

(56) References Cited

U.S. PATENT DOCUMENTS

| 5,493,109 A | * 2/1996 | Wei ........................ A61B 3/102 |
| | | 250/201.3 |
| 6,325,512 B1 | 12/2001 | Wei |
| 2012/0184846 A1 | 7/2012 | Izatt et al. |
| 2012/0274783 A1 | 11/2012 | Ko et al. |
| 2014/0221822 A1 | 8/2014 | Ehlers et al. |

FOREIGN PATENT DOCUMENTS

| EP | 0697611 A2 | 2/1996 |
| WO | 2006/105903 A2 | 10/2006 |

OTHER PUBLICATIONS

International Searching Authority, International Search Report, May 27, 2016, 5 pgs.

\* cited by examiner

*Primary Examiner* — Hung Dang

(57) ABSTRACT

An OCT tracking system includes an imaging unit operable to generate a fundus image of a patient's eye and a tracking system operable to process the fundus image to determine a location of a surgical instrument inserted into the patient's eye. The OCT tracking system further includes an OCT system including an OCT light source operable to generate an OCT imaging beam and a beam scanner. Based at least in part on the determined location of the surgical instrument, the beam scanner directs the OCT imaging beam to a particular region within the patient's eye, the particular region within the patient's eye including the determined location of the surgical instrument inserted into the patient's eye.

11 Claims, 4 Drawing Sheets

TRACKING SYSTEM FOR SURGICAL OPTICAL COHERENCE TOMOGRAPHY

FIELD

The present disclosure relates generally to improved visualization for vitreo-retinal, glaucoma, or other ophthalmic surgeries and, more particularly, to a tracking system for surgical optical coherence tomography (OCT).

BACKGROUND

Imaging and visualization techniques for assisting ophthalmic surgeons are becoming increasingly popular, and much research and development is being conducted regarding these techniques. One class of ophthalmic surgeries, the vitreo-retinal procedure, involves vitrectomy, the removal of the vitreous body from the posterior chamber to access the retina. The successful execution of vitrectomy requires an essentially complete removal of the vitreous, including the most challenging regions near the vitreous base. Using imaging techniques and devices can be of substantial help to improve the efficiency of the vitreous removal.

However, assisting vitrectomy with imaging is particularly challenging for several reasons. One of them is that the vitreous is transparent. Another challenge is that visualization of the periphery requires imaging beams with a high angle of obliqueness. Similar visualization issues exist during membrane peeling procedures. At present, typically microscope or video-microscope imaging is used to address the former challenge, and wide angle contact-based or non-contact based lenses are used to address the latter challenge, in each case with limited success.

Improvement of the imaging can be achieved by using optical coherence tomography (OCT), a technique that enables visualization of the target tissue in depth by focusing a laser beam onto the target, collecting the reflected beam, interfering the reflected beam with a reference beam and detecting the interference, and measuring the reflectance signature within the depth of focus of the beam. The result is a line scan in depth, a cross-sectional scan, or a volumetric scan.

Conventional diagnostic ophthalmic OCT systems use retinal tracking to track the motion of the retina. In such system, an initial fundus image may be acquired by a fundus imager and set as a reference. Sequential fundus images may be taken in real-time and compared to the reference fundus image to track the relative motion of the retina, which is then used as a feedback to the OCT scanner so that the OCT system is always tracking and scanning the same area of the retina. However, scanning a fixed and predetermined area does not necessarily provide the useful information surgeons may need as, during surgery, surgeons are often more concerned about those area directly underneath or close to the surgical instrument. Accordingly, certain embodiment of the present disclosure may beneficially provide an OCT system that that facilities increased surgeon control over the scanning location.

SUMMARY

In certain embodiments, an OCT tracking system includes an imaging unit operable to generate a fundus image of a patient's eye and a tracking system operable to process the fundus image to determine a location of a surgical instrument inserted into the patient's eye. The OCT tracking system further includes an OCT system including an OCT light source operable to generate an OCT imaging beam and a beam scanner. Based at least in part on the determined location of the surgical instrument, the beam scanner directs the OCT imaging beam to a particular region within the patient's eye, the particular region within the patient's eye including the determined location of the surgical instrument inserted into the patient's eye.

Certain embodiments of the present disclosure may provide one or more technical advantages. For example, the ability to generate real-time OCT scans in the vicinity of the surgical instrument in accordance with the present disclosure may provide more useful information to a surgeon as compared to scans from a predetermined location in which the surgeon may not be working at a given time. Accordingly, embodiments of the present disclosure may make intra-operative OCT more convenient for the surgeon.

BRIEF DESCRIPTION OF THE DRAWINGS

For a more complete understanding of the present disclosure and the advantages thereof, reference is now made to the following description taken in conjunction with the accompanying drawings in which like reference numerals indicate like features and wherein.

Figure 1:
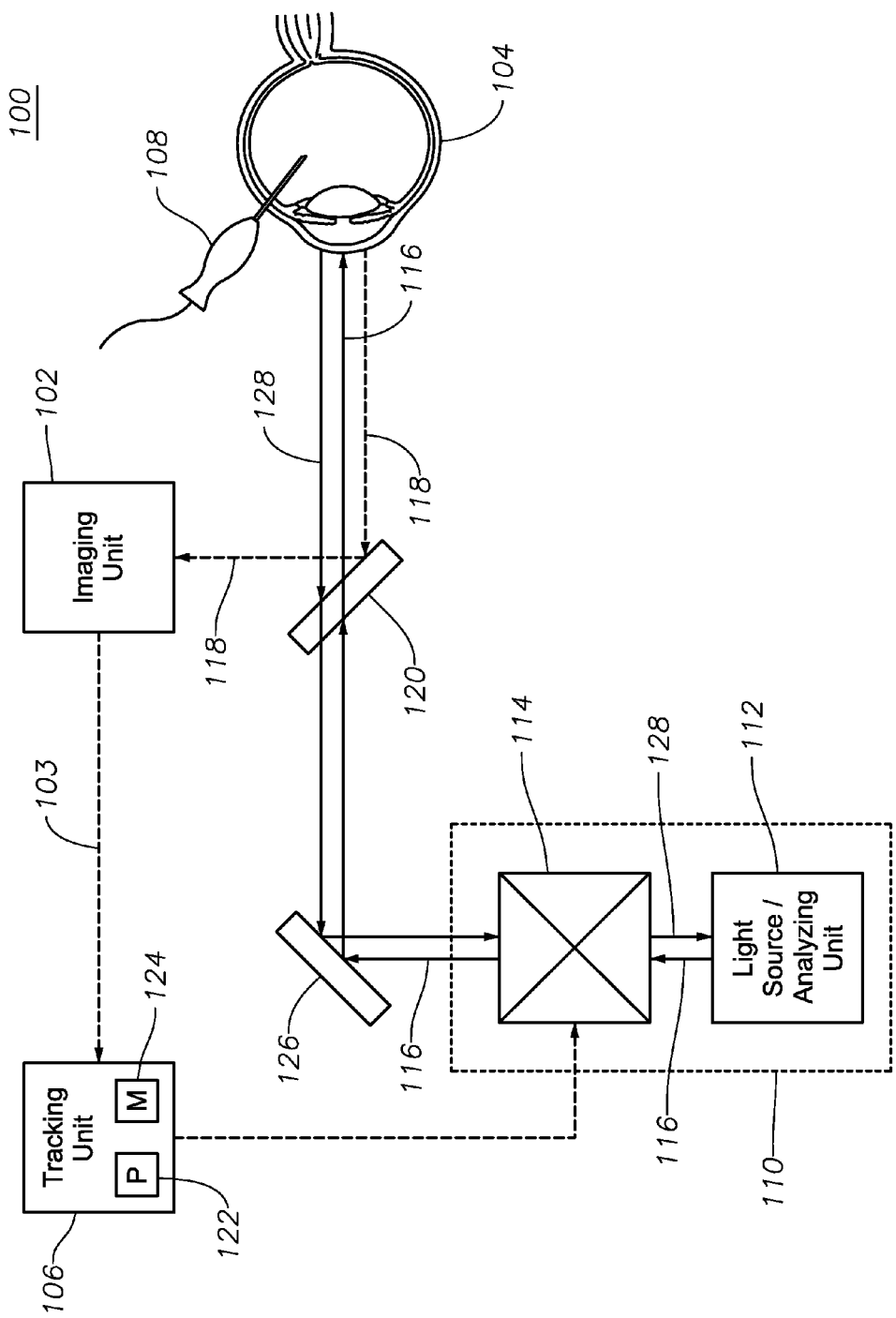
FIG. 1 illustrates an exemplary OCT tracking system, according to certain embodiments of the present disclosure.

The skilled person in the art will understand that the drawings, described below, are for illustration purposes only. The drawings are not intended to limit the scope of the applicant's disclosure in any way.

DETAILED DESCRIPTION

For the purposes of promoting an understanding of the principles of the present disclosure, reference will now be made to the embodiments illustrated in the drawings, and specific language will be used to describe the same. It should nevertheless be understood that no limitation of the scope of the disclosure is intended. Any alterations and further modifications to the described systems, devices, and methods, and any further application of the principles of the present disclosure are fully contemplated as would normally occur to one skilled in the art to which the disclosure relates. In particular, it is fully contemplated that the systems, devices, and/or methods described with respect to one embodiment may be combined with the features, components, and/or steps described with respect to other embodiments of the present disclosure. For the sake of brevity, however, the numerous iterations of these combinations will not be described separately. For simplicity, in some instances the same reference numbers are used throughout the drawings to refer to the same or like parts.

In general, the present disclosure may provide an OCT tracking system that includes a fundus imaging unit, a tracking unit, and an OCT system. The tracking unit is operable to process a fundus image generated by the fundus imaging unit to determine a location of a surgical instrument within a patient's eye during surgery. The determined location of the surgical instrument may be used by a beam scanner of the OCT system to direct the location of an OCT imaging beam within the patients eye (e.g., to a region of the patient's eye in which the surgical instrument is located). As a result, OCT images may be generated in the same vicinity as the surgical instrument, and the OCT images may track the surgical instrument as it moves within the patient's eye (as opposed to the OCT images being of a predetermined location within the patient's eye in the case of a system that merely tacks the retina during use). A system in which the OCT images track a surgical instrument during surgery, as disclosed herein, may be beneficial as a surgeon is often most concerned about the structures within the eye in the immediate vicinity of the surgical instrument.

FIG. 1 illustrates an exemplary OCT tracking system 100, according to certain embodiments of the present disclosure. In general, OCT tracking system 100 includes an imaging unit 102 for generating a fundus image 103 of a patient's eye 104 during surgery and a tracking unit 106 for processing fundus images 103 generated by imaging unit 102 in order to determine a location of a surgical instrument 108 (e.g., a vitrectomy probe, a laser probe, a forceps or any other suitable surgical instrument) in those fundus images 103. OCT tracking system 100 further includes an OCT system 110 comprising a light source/analyzing unit 112 and a beam scanner 114. Light source/analyzing unit 112 generates an OCT imaging beam 116, and beam scanner 114 directs the generated OCT imaging beam 116 to a particular region within the patient's eye 104. Beam scanner 114 is communicatively coupled to tracking unit 106 such that the particular region to which the OCT imaging beam 116 is directed can be determined based at least in part on the location of surgical instrument 108. Reflections of the OCT imaging beam 116 from the particular region within the patient's eye 104 may return to light source/analyzing unit 112 along the same optical path as OCT imaging beam 116, and light source/analyzing unit 112 may generate real-time, cross sectional OCT images of the particular region by determining interference between the reflections and a reference arm of the OCT imaging beam 116. As a result, OCT tracking system 100 may facilitate real-time OCT imaging that tracks the movement of a surgical instrument 108 during surgery.

Imaging unit 102 of OCT tracking system 100 may include any suitable device for generating a fundus image 103 of a patient's eye 104 and may include suitable magnification and focusing optics (not depicted) for performing that function. As a simplified example, visible or near infrared light 118 from the patient's eye 104 may be directed toward imaging unit 102 via a mirror 120 operable to reflect or partially reflect wavelengths in the visible or near infrared spectrum. In certain embodiment, fundus images 103 may be discrete still photographs of the patient's eye 104. In other embodiment, the fundus image 103 may comprise a continuous video stream of the patient's eye 104. Example imaging units may include digital video cameras, line scan ophthalmoscopes or confocal-scanning ophthalmoscopes.

Tracking unit 106 of ophthalmic illumination system 100 may be generally operable to determine the location of surgical instrument 108 within the patient's eye 104 based at least in part on fundus images 103 generated by imaging unit 102. Tracking unit 106 may include any suitable combination of hardware, firmware, and software. In certain embodiments, tracking unit 106 may include a processing module 122 and a memory module 124. Processing module 122 may include one or more microprocessors, field-programmable gate arrays (FPGAs), controllers, or any other suitable computing devices or resources. Processing module 122 may work, either alone or with other components of OCT tracking system 100, to provide the functionality described herein. Memory module 124 may take the form of volatile or non-volatile memory including, without limitation, magnetic media, optical media, random access memory (RAM), read-only memory (ROM), removable media, or any other suitable memory component.

Tracking unit 106 may be programmed to (or may store software in memory module 124 that, when executed by processing module 122, is operable to) process the fundus images 103 generated by imaging unit 102 to determine and track the location of surgical instrument 108 within the patient's eye 104. For example, the processing module 122 may receive and process the images acquired by the imaging unit 102. The memory module 124 of the tracking unit 106 may store the pre-processed and/or post-processed image data. The processing module 122 may detect and calculate the location and/or orientation (or the change of the location and orientation) of the surgical instrument 108 in the surgical field based on the fundus images.

Tracking unit 106 may be communicatively coupled (via wired or wireless communication) to OCT system 110, and tracking unit 106 may be programmed to (or may store software in memory module 124 that, when executed by processing module 122, is operable to) generate signals to be communicated to OCT system 110 to cause beam scanner 114 of OCT system 110 to direct the location of the OCT imaging beam 116 within the patient's eye 104. The signals may be generated based on the determined location of the surgical instrument 108 within the patient's eye 104 and, possibly, user input from a surgeon (which may be received via a graphical user interface (GUI) or other suitable input device). The control of beam scanner 114 by tracking unit 106 will be described in further detail below. Although tracking unit 106 is primarily described as controlling beam scanner 114, the present disclosure contemplate that, alternatively, beam scanner 114 may itself include any suitable combination of hardware, firmware, and software facilitating tracking of a surgical instrument 108 based on fundus images 103 generated by imaging unit 102.

OCT system 110 of OCT tracking system 100 may include a light source/analyzing unit 112 and beam scanner 114. OCT system 110 may include any suitable additional optical components for manipulating OCT imaging beam 116 as would be understood by those of skill in the art, and those additional components are not depicted/described for the sake of simplicity. As one example, the OCT imaging beam 116 may comprise an infrared or near infrared light beam covering a relatively narrow band of wavelengths (e.g., 830 nm-870 nm, 790 nm-900 nm, 950 nm-1150 nm). However, an OCT imaging beam 116 having any suitable spectral range may be used. The OCT imaging beam 116 may pass through beam scanner 114 (described in further detail below) along with any other suitable optical components of OCT system 100 (not depicted, as described above). OCT imaging beam 116 may then be directed to the patient's eye 104, such as by a mirror 126 operable to reflect light falling within the spectral range of the OCT imaging beam 116. Additionally, mirror 120 may be a mirror that allows light falling within the spectral range of the OCT imaging beam 116 to pass through such that the OCT imaging beam 116 may reach the patient's eye 104. In an alternative embodiment, mirror 126 may be placed between mirror 120 and the patient's eye 104 in FIG. 1. In this case, mirror 126 may be a mirror that allows light 118 to pass through and allows the OCT imaging beam 116 to be reflected to image the patient's eye 104.

Beam scanner 114 may comprise any suitable optical component or combination of optical components facilitating focusing of the OCT imaging beam in the X-Y plane. For example, beam scanner 114 may include one or more of a pair of scanning mirrors, a micro-mirror device, a MEMS based device, a deformable platform, a galvanometer-based scanner, a polygon scanner, and/or a resonant PZT scanner.

In certain embodiments, the position of the optical components of beam scanner 114 may be manipulated in an automated manner (e.g., based on the above-described signals generated by tracking unit 106) in order to control the region of the patient's eye 104 to which OCT imaging beam 116 is directed. As just one example, beam scanner 114 may comprise a pair of scanning mirrors each coupled to a motor drive, the motor drives operable to rotate the mirrors about perpendicular axes. As a result, by controlling the position of the coupled motors (e.g., via the above-described signal), the X-Y positioning of OCT imaging beam 116 within the patient's eye 104 can be controlled.

A portion of the OCT imaging beam 116 reaching the patient's eye 104 may be reflected by the patient's eye (reflected OCT beam 128). Reflected OCT beam 128 may return to OCT system 110 along substantially the same optical path as traveled by OCT imaging beam 116. Once reflected OCT beam 128 reaches light source/analyzing unit 112, light source/analyzing unit 112 may construct an OCT image based on interference between the reflected OCT beam 128 and a reference arm of OCT imaging beam 116 (as is known in the art).

As described above, tracking unit 106 may generate signals to be to control the operation of beam scanner 114 and the thus location of the OCT imaging beam 116 within the patient's eye 104. The signals may be generated based on the determined location of the surgical instrument within the patient's eye 106 (as determined by tracking unit 106 based on fundus images 103 generated by imaging unit 102, as described above). Additionally, the signals may be generated based on user input from a surgeon. Such user input may indicate the "mode" by which the live, cross-sectional OCT scans will track the surgical instrument 108. For example, user input may indicate a desire to control beam scanner 114 according to a tracking mode (as described below with regard to FIGS. 2A-2C). As another example, user input may indicate a desire to control beam scanner 114 according to a drag and drop mode (as described below with regard to FIGS. 3A-3C). As yet another example, user input may indicate a desire to totally disable the instrument tracking feature. Instead, the imaging unit 102 may track the motion of the fundus and guide the OCT system 110 to image a fixed (but retinal-tracked) region of the patient's eye.

Figure 2:
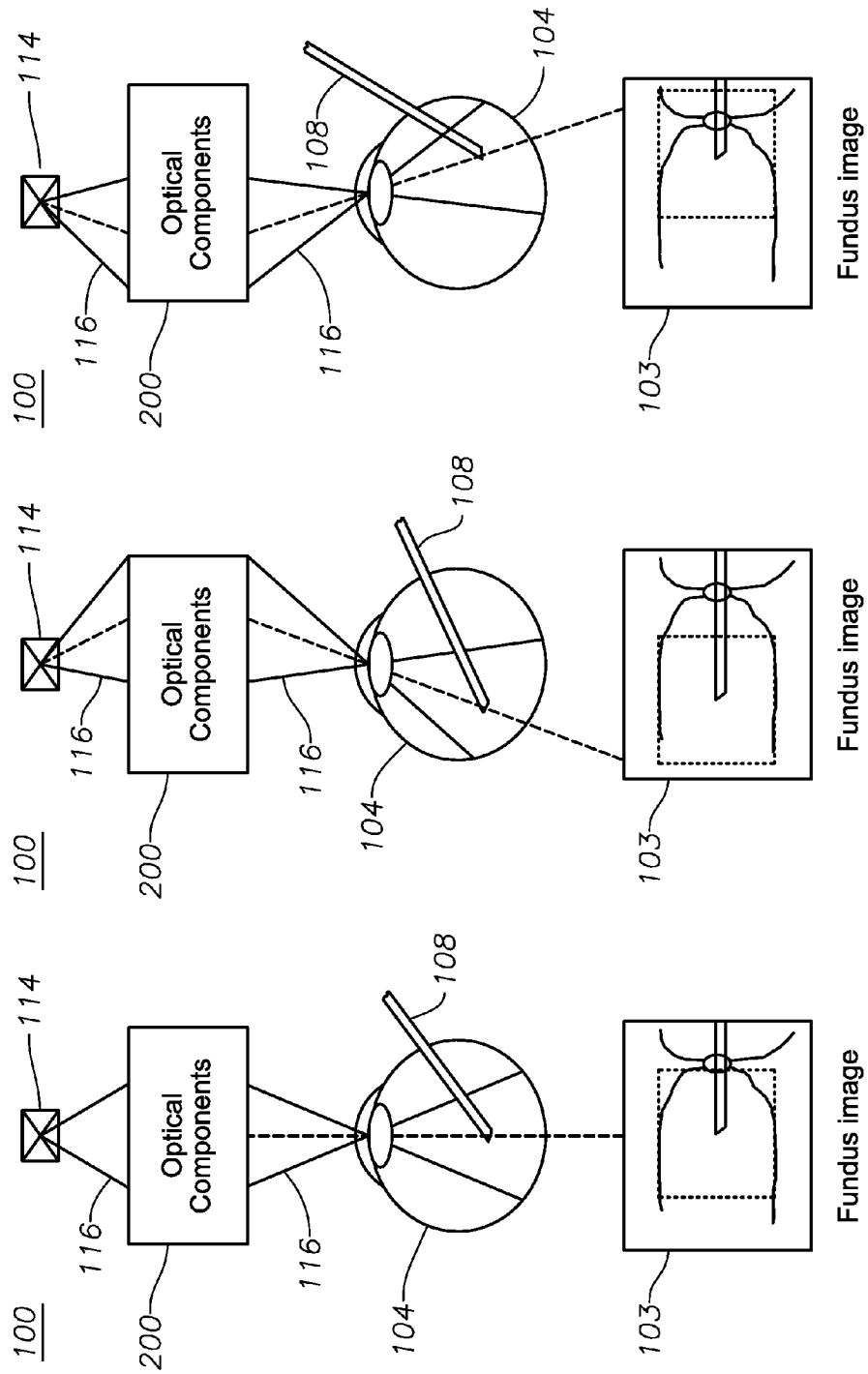
FIGS. 2A-2C illustrate a simplified version of the OCT tracking system depicted in FIG. 1 operating in a tracking mode, according to certain embodiments of the present disclosure.

FIGS. 2A-2C illustrate a simplified version of OCT tracking system 100 operating in a tracking mode, according to certain embodiments of the present disclosure. Although, for purposes of simplicity, certain components of OCT tracking system 100 have not been reproduced and other components are depicted in a consolidated manner as optical components 200 (e.g., mirror 126 along with any other non-depicted components for focusing OCT imaging beam 116 in the patient's eye 104) for purposes of simplicity, the present disclosure contemplates that the OCT tracking system 100 depicted in FIGS. 2A-2C is substantially the same as that shown in FIG. 1.

In the illustrated tracking mode, tracking unit 106, having determined the position of surgical instrument 108 in successive fundus images 103, may generate signals for controlling the positioning of beam scanner 114. The generated signals may cause beam scanner 114 to direct OCT imaging beam 116 such that, at any given point in time, it is directed within the patient's eye 104 to an area in which the tip of the surgical instrument 108 is located. In one embodiment, the relative position between the surgical instrument tip and the scanning area is always maintained.

Figure 3:
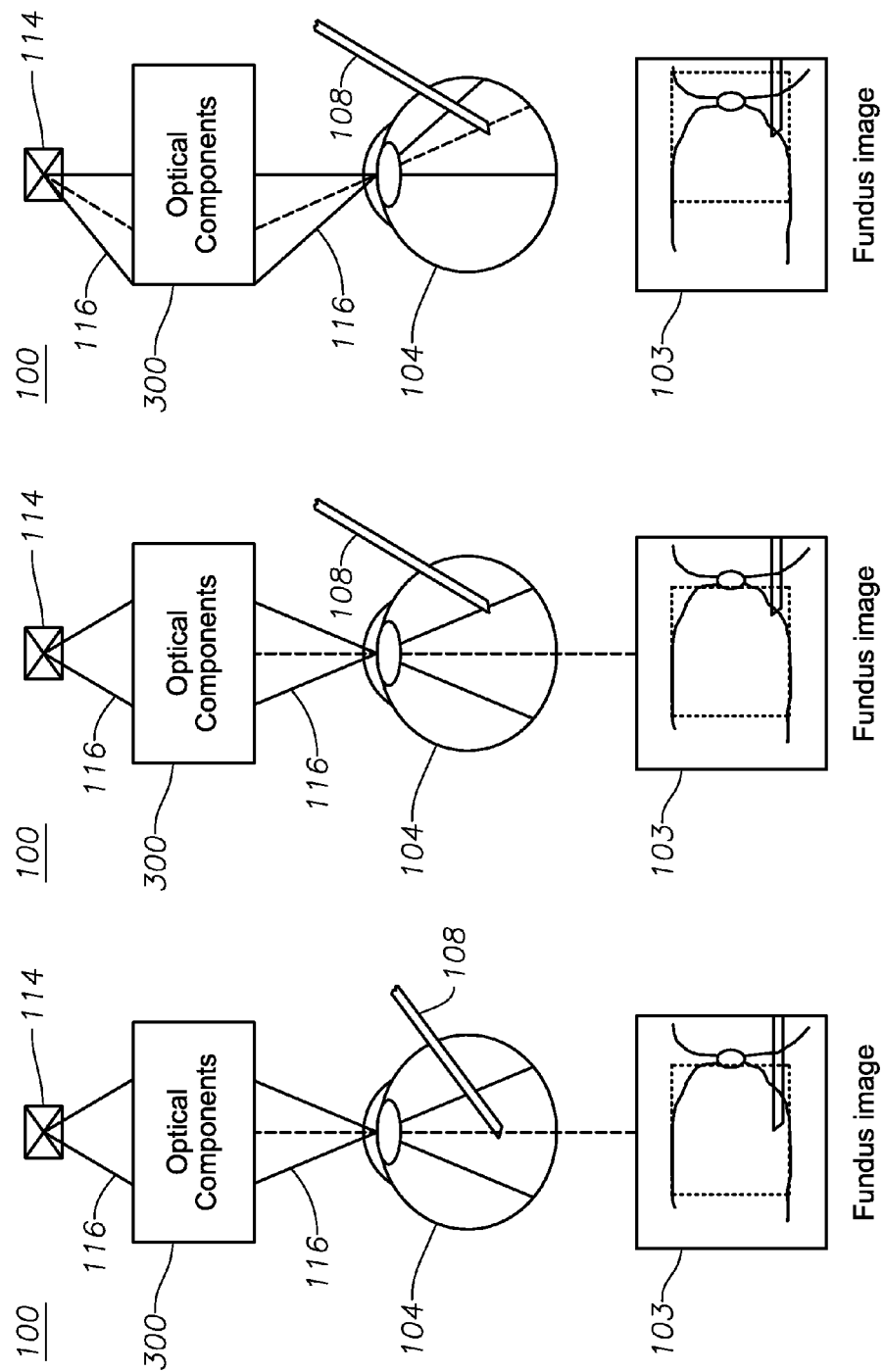
FIGS. 3A-3C illustrate a simplified version of the OCT tracking system depicted in FIG. 1 operating in a drag and drop mode, according to certain embodiments of the present disclosure.

FIGS. 3A-3C illustrate a simplified version of OCT tracking system 100 operating in a drag and drop mode, according to certain embodiments of the present disclosure. Although, for purposes of simplicity, certain components of OCT tracking system 100 have not been reproduced and other components are depicted in a consolidated manner as optical components 300 (e.g., mirror 126 along with any other non-depicted components for focusing OCT imaging beam 116 in the patient's eye 104) for purposes of simplicity, the present disclosure contemplates that the OCT tracking system 100 depicted in FIGS. 3A-3C is substantially the same as that shown in FIG. 1.

In the illustrated drag and drop mode, tracking unit 106 may only generate signals for controlling the positioning of beam scanner 114 in response to user input from the surgeon. In other words, beam scanner 114 may direct OCT imaging beam 116 to a set location within the patient's eye regardless of the position of the surgical instrument 108 in the absence of user input from the surgeon (as depicted in FIGS. 2A-2B). However, if an input is received by tracking unit 106 indicating the desire of the surgeon to move the set location at which the OCT imaging beam is focused, tracking unit 106 may generate signals facilitating tracking like that described with regard to FIGS. 2A-2C (but only for the duration during which the input is continuously received). As a result, the surgeon may have the ability to "drag and drop" the set location at which OCT images are generated. In another embodiment, in the absence of user input from the surgeons (as depicted in FIGS. 2A-2B), the tracking unit 106 may operate in a "retinal" tracking mode. In other words, the tracking unit 106 may track the motion of the retina (instead of the surgical tool) and generate signals for controlling the positioning of the beam scanner 114 to deliver OCT imaging beam 116 to a set location on retina (within the patient's eye) with a pre-set scan pattern, such as a line scan, circular scan, cubical scan, raster scan, spiral scan or star-shape scan etc. Similarly, if an input is received by tracking unit 106 indicating the desire of the surgeon to move the set location at which the OCT imaging beam is focused, tracking unit 106 may generate signals facilitating tracking like that described with regard to FIGS. 2A-2C (but only for the duration during which the input is continuously received). As a result, the surgeon may have the ability to "drag and drop" the set location at which OCT images are generated.

Figure 4:
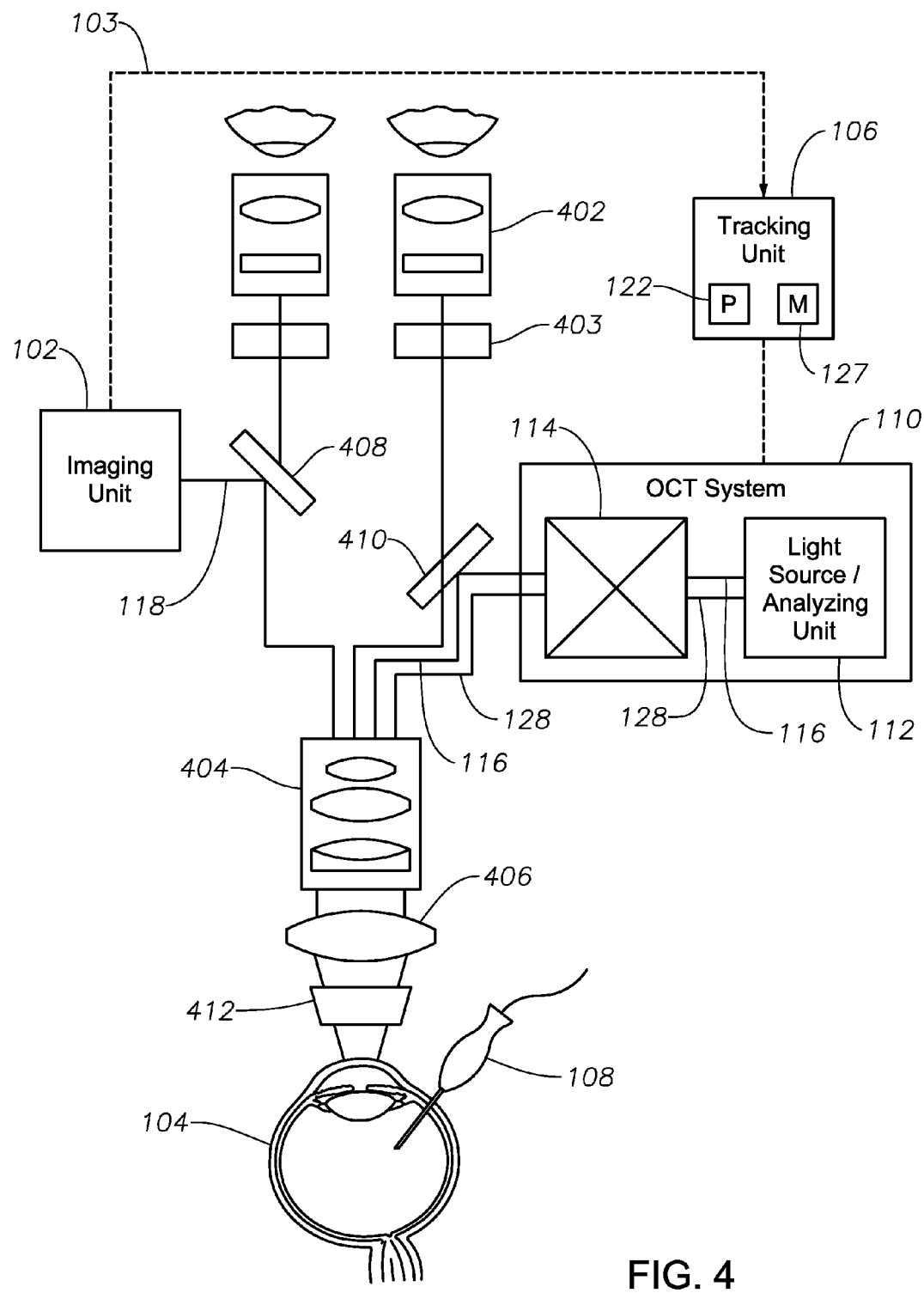
FIG. 4 illustrates an exemplary ophthalmic surgical microscope having an integrated OCT tracking system, according to certain embodiments of the present disclosure.

FIG. 4 illustrates an exemplary ophthalmic surgical microscope 400 having an integrated OCT tracking system, according to certain embodiments of the present disclosure. Because components of the OCT tracking system integrated into surgical microspore 400 may be substantially the same as described with regard to FIG. 1 and OCT tracking system 100, the same reference numerals are used with regard to FIG. 4.

Ophthalmic surgical microscope 400 may generally include eyepieces 402, relay lens 403, magnifying/focusing optics 404, an objective lens 406, and a surgical viewing optics 412, each of which may include any suitable optical components as understood by persons of ordinary skill in the art. A portion of the light passing along the optical path of the surgical microscope 400 may be directed to imaging unit 102 via a beam splitter 408, and, based on that portion of light, imaging unit 102 may generate the fundus image 103. Beam splitter 408 may include a planar mirror, a splitter cube, or any other suitable optical device for redirecting a portion of the light passing through ophthalmic surgical microscope 400. In certain embodiments, beam splitter 408 may be located along the optical path between the objective lens 406 and an eyepiece 402. More particularly, beam splitter 408 may be located along the optical path between magnifying/focusing optics 404 and an eyepiece 402 (such that the fundus image 103 corresponds to what the surgeon is viewing through ophthalmic surgical microscope 400).

The OCT imaging beam 116, which is generated by light source/analyzing unit 112 and directed by beam scanner 114 as described above, may be directed along a portion of the optical path of the surgical microscope via a beam coupler 410. Beam coupler 410 may include an optical element configured to reflect wavelengths in the spectral range of the OCT imaging beam 116 (e.g., infrared wavelengths) while allowing passage of light in the visible spectrum passing through ophthalmic surgical microscope 400. In certain embodiments, beam coupler 410 may be located along the optical path between the surgical viewing optics 412 and an eyepiece 402. Surgical viewing optics 412 can be a drop-on macular lens, contact-based wide-angle lens, noncontact-based viewing system such as (binocular indirect ophthalmomicroscope) BIOM, or any other suitable viewing optics. More particularly, beam coupler 410 may be located along the optical path between magnifying/focusing optics 404 and an eyepiece 402. Additionally, OCT system 110 may include suitable optical components (not depicted) such that appropriate focus of OCT imaging beam 116 within the patient's eye 104 is achieved in light of the fact that the OCT imaging beam 116 passes through magnifying/focusing optics 404 and objective lens 406.

It will be appreciated that various of the above-disclosed and other features and functions, or alternatives thereof, may be desirably combined into many other different systems or applications. It will also be appreciated that various presently unforeseen or unanticipated alternatives, modifications, variations or improvements therein may be subsequently made by those skilled in the art which alternatives, variations and improvements are also intended to be encompassed by the following claims.

What is claimed is:

1. An OCT tracking system, comprising:
 an imaging unit operable to generate a fundus image of a patient's eye;
 a tracking system operable to:
  process the fundus image to determine a location of a surgical instrument inserted into the patient's eye; and
  receive a user input for a period of time; and
 an OCT system comprising:
  an OCT light source operable to generate an OCT imaging beam; and
  a beam scanner operable, based at least in part on the determined location of the surgical instrument and only during the period of time, to direct the OCT imaging beam to a particular region within the patient's eye, the particular region within the patient's eye including the determined location of the surgical instrument inserted into the patient's eye.

2. The system of claim 1, wherein the OCT system is operable to generate an OCT image of the particular region of the patient's eye based at least in part on a portion of the OCT imaging beam reflected by the patient's eye.

3. The system of claim 1, further comprising a surgical microscope including first and second eyepieces and an objective lens, wherein:
 the imaging unit is operable to generate the fundus image based on a portion of light passing along the optical pathway of the surgical microscope, the portion of light being reflected by a beam splitter between surgical viewing optics and one of the first and second eyepieces of the surgical microscope; and
 the OCT imaging beam is directed along a portion of the optical path of the surgical microscope via a beam coupler, the beam coupler positioned along the optical path between the surgical viewing optics and one of the first and second eyepieces.

4. The system of claim 1, wherein:
 the tracking system is further operable to generate signals to be communicated to the beam scanner, the signals based at least in part of the determined location of the surgical instrument; and
 the beam scanner directs the OCT imaging beam to a particular region within the patient's eye in response to the signals.

5. The system of claim 1, wherein the surgical instrument comprises one of a vitrectomy probe and a laser probe.

6. The system of claim 1, wherein the imaging unit comprises at least one of a 2-dimesional camera, a line-scan camera, and a single detector as those used in con-focal scanning ophthalmoscope.

7. An ophthalmic surgical microscope, comprising:
 an imaging unit operable to generate a fundus image of a patient's eye based on a portion of light passing along the optical pathway of the ophthalmic surgical microscope, the portion of light being reflected by a beam splitter between surgical viewing optics for the ophthalmic surgical microscope and one of a first and a second eyepiece of the ophthalmic surgical microscope;
 a tracking system operable to:
  process the fundus image to determine a location of a surgical instrument inserted into the patient's eye; and
  receive a user input for a period of time; and
 an OCT system comprising:
  an OCT light source operable to generate an OCT imaging beam; and
  a beam scanner operable, based at least in part on the determined location of the surgical instrument and only during the period of time, to direct the OCT imaging beam to a particular region within the patient's eye, the particular region within the patient's eye including the determined location of the surgical instrument inserted into the patient's eye, the OCT imaging beam being directed to the particular region within the patient's eye along a portion of the optical path of the surgical microscope via a beam coupler, the beam coupler positioned along the optical path between the surgical viewing optics for the ophthalmic surgical microscope and one of the first and second eyepieces of the ophthalmic surgical microscope.

8. The ophthalmic surgical microscope of claim 7, wherein the OCT system is operable to generate an OCT image of the particular region of the patient's eye based at least in part on a portion of the OCT imaging beam reflected by the patient's eye.

9. The ophthalmic surgical microscope of claim 7, wherein:

the tracking system is further operable to generate signals to be communicated to the beam scanner, the signals based at least in part of the determined location of the surgical instrument; and the beam scanner directs the OCT imaging beam to a particular region within the patient's eye in response to the signals.

10. The ophthalmic surgical microscope of claim 7, wherein the surgical instrument comprises one of a vitrectomy probe and a laser probe.

11. The ophthalmic surgical microscope of claim 7, wherein the imaging unit comprises at least one of a 2-dimesional camera, a line-scan camera, and a single detector as those used in con-focal scanning ophthalmoscope.

* * * * *